United States Patent [19]

Goulding

[11] Patent Number: 5,072,737
[45] Date of Patent: Dec. 17, 1991

[54] METHOD AND APPARATUS FOR METABOLIC MONITORING

[75] Inventor: Peter Goulding, San Diego, Calif.

[73] Assignee: Puritan-Bennett Corporation, Carlsbad, Calif.

[21] Appl. No.: 336,724

[22] Filed: Apr. 12, 1989

[51] Int. Cl.⁵ ............................................. A61B 5/08
[52] U.S. Cl. .................................... 128/718; 128/719; 128/725; 128/205.23; 73/23.2
[58] Field of Search ............... 128/633, 716, 719, 718, 128/725, 726, 205.23, 664, 665, 720; 73/16, 23.1, 861, 430, 23.2, 23.21, 23.5, 31.01

[56] References Cited

U.S. PATENT DOCUMENTS

| | | | |
|---|---|---|---|
| 3,507,146 | 4/1970 | Webb | 128/718 |
| 3,514,377 | 5/1970 | Spacil et al. | 128/719 |
| 3,799,149 | 3/1974 | Rummel et al. | 128/718 |
| 3,895,630 | 7/1975 | Bachman | 128/718 |
| 3,946,729 | 3/1976 | Hanna | 128/145.8 |
| 4,163,450 | 8/1979 | Kirk et al. | 128/145.8 |
| 4,178,919 | 12/1979 | Hall | 128/719 |
| 4,197,857 | 4/1980 | Osborn | 128/718 |
| 4,233,842 | 11/1980 | Raemer et al. | 73/861.04 |
| 4,368,740 | 1/1983 | Binder | 128/718 |
| 4,413,632 | 11/1983 | Schlessinger et al. | 128/716 |
| 4,423,739 | 1/1984 | Passaro et al. | 128/719 |
| 4,448,058 | 5/1984 | Jaffe et al. | 128/719 |
| 4,459,982 | 7/1984 | Fry | 128/204.23 |
| 4,578,767 | 3/1986 | Wong | 128/719 |
| 4,608,995 | 9/1986 | Linnarsson et al. | 128/719 |
| 4,619,269 | 10/1986 | Cutler et al. | 128/718 |
| 4,856,531 | 8/1989 | Merilainen | 128/719 |

FOREIGN PATENT DOCUMENTS

| | | | |
|---|---|---|---|
| 1915959 | 10/1970 | Fed. Rep. of Germany | 128/719 |
| 0284257 | 12/1986 | Japan | 128/719 |
| 829409 | 3/1960 | United Kingdom | 128/719 |

Primary Examiner—David J. Isabella
Assistant Examiner—K. Reichle
Attorney, Agent, or Firm—Fulwider, Patton, Lee & Utecht

[57] ABSTRACT

A method and apparatus for measuring metabolic rates such as oxygen consumption and carbon dioxide elimination rates of a patient intubated on a ventilator utilize an inspiration sample of gases provided by the ventilator and end-tidal and ambient pressure samples of expiration gases exhaled by the patient which are collected and analyzed to determine concentrations of the gases along with flow rate data to calculate the desired metabolic rates on a breath-by-breath flow weighted average basis. The ambient pressure sample is taken from a point prior to complete mixing of the gases exhaled in adjacent breaths and after the exhalation valve such that the pressure is essentially ambient room air pressure to facilitate accurate sychronization of the flow rate and concentration signals.

19 Claims, 1 Drawing Sheet

METHOD AND APPARATUS FOR METABOLIC MONITORING

BACKGROUND OF THE INVENTION

1. Field of the Invention

The present invention relates generally to the field of medicine, and more particularly to a method and apparatus for monitoring the metabolic rate of a patient intubated on a ventilator.

2. Description of the Related Art

There are many medical conditions which require that a patient receive assistance in breathing. Such breathing assistance may be provided, for example, by an electromechanical ventilator. A model 7200a ventilator manufactured by Puritan-Bennett Corporation, the assignee of the present patent application, is representative of such devices. The ventilator includes an inspiration conduit that carries inspiration gases such as air or oxygen to the patient and an expiration conduit that carries expired gases from the patient back to the ventilator. These two conduits are typically connected to a "wye" fitting which forms a part of a patient airway adapted to facilitate the flow of the various gases to and from the lungs of the patient through a trachea tube.

The ventilator is adapted to provide certain respiratory information such as inspired and expired flow rates and pressures. However, other information not provided by the ventilator is sometimes required for various medical purposes. In particular, this required information includes the rates at which the patient consumes oxygen and eliminates carbon dioxide, preferably on a breath-by-breath basis.

It has been proposed that breath-by-breath oxygen and carbon dioxide rates be obtained from measurements of the concentration of these gases in the patient airway. According to this approach, a sample conduit would be connected to the wye. A sample of the gases in the wye would be carried through the sample conduit to a set of sensors for measurement of the concentrations of oxygen and carbon dioxide. A flowmeter in the sample conduit would provide flow data which would be used to synchronize the measured concentrations with the flow of the gases in the airway. Flow rate and pressure information from the ventilator would be used to compute inspired and expired flow rates and volumes. All of this information would be corrected for temperature and humidity and would then be used to calculate the required oxygen consumption and carbon dioxide elimination rates.

This proposal has been found to require highly complex mathematical algorithms, particularly in correcting for compliance flow in the conduits. Most devices (ventilators) measure flow at a distance from the patient. Measuring metabolics at the wye either requires an additional flowmeter located at the wye or an extrapolation of flow by distant transducers requiring eliminating compliance flow. Moreover, synchronization of the measured concentrations with the flow is required due to the length of time required for a given sample of gas to flow through the sample conduit from the wye to the sensors, but this sychronization is subject to errors due to patient pressure fluctuations, condensation of $H_2O$ in the line, obstruction of the line by mucous, kinks or even leaks in the line. The error margin for this synchronization is small because the concentration profiles make a rapid transistion from inspiration to expiration causing a step change which when integrated will cause substantial error if misaligned.

Finally, the response time of the sensors is so critical that a relatively slow response from a sensor can substantially affect the measurement. These problems have made it impractical to implement the breath-by-breath determination of oxygen and carbon dioxide rates by sampling the gases in the wye.

It is possible to determine average oxygen and carbon dioxide rates by means of a mixing chamber in which exhaled gas is captured and held over several breaths. Two sample lines are required—one connected to the wye for measurement of concentrations in the inspiration gases and for waveform analysis, and one connected downstream from the mixing chamber for measurement of concentrations of expired gases. A solenoid valve is used to switch the sensors between the two sample lines. Although this system provides oxygen and carbon dioxide rates, it cannot do so on a breath-by-breath basis. In addition, the mixing chamber is physically bulky and can be difficult to sterlize.

A mixing chamber system is non-functional if the concentration profile exiting the chamber is anything but flat (constant concentration). Therefore, these systems are limited by ventilation rates that "wash-out" the mixing chamber. Continuous flow ventilation is one application in which mixing chamber systems are normally ineffective. A large mixing chamber would be able to handle continuous flow and rapid ventilation, however would also be very insensitive to actual patient changes, thus decreasing its effectiveness.

It will be apparent from the foregoing that there is a need for a way to accurately determine breath-by-breath oxygen consumption and carbon dioxide production rates of a patient on a ventilator.

SUMMARY OF THE INVENTION

The present invention provides a method and apparatus for accurately monitoring breath-by-breath flow-weighted average metabolic rates, for example, oxygen consumption and carbon dioxide elimination by a patient intubated on a ventilator.

Briefly and in general terms, a novel metabolic monitor according to the invention includes conduits for collecting a sample of inspiration gases and an end-tidal sample of expiration gases. The ambient pressure sample is collected from a point prior to complete mixing of the gases exhaled in adjacent breaths and after the exhalation valve in the patient tubing such that the ambient pressure sample allows the synchronization of flow and concentration to be constant with regard to patient pressure fluctuations. The location of the sample line is less susceptible to mucous (after a filter) and less likely to kink (not draped across the patient). The choice of sample line is tubing formed from a perfluorosulfonic acid membrane sold under the trademark "NAFION" which prevents $H_2O$ condensation problems. Therefore the synchronization is less problematic. It is also less sensitive to error because the concentration profiles do not change as rapidly due to partial mixing, causing the integration error to be smaller when misaligned. The pressure is essentially ambient room air pressure. A selector selects one of the samples for analysis and a sensor provides a signal indicative of a parameter of the selected sample.

Preferably two sensors are used, one to sense oxygen concentration and the other to sense carbon dioxide concentration. Each of the samples is analyzed and a computer uses the oxygen and carbon dioxide concentrations of the sample together with flow rate data to compute breath-by-breath flow weighted averages of the rates of oxygen consumption and carbon dioxide elimination.

In one embodiment the selector comprises a fluid flow control valve which establishes fluid communicating between the sensor and the conduit carrying the selected sample. The computer controls the valve, and the entire process of collecting and analyzing the samples and computing the desired metabolic rates carried out automatically under control of the computer.

According to the present invention a method of measuring metabolics is provided that utilizes apparatus of the kind described above. The method comprises the steps of collecting the sample of inspiration gases and the end-tidal and ambient pressure samples of expiration gases, selecting one of the sample for analysis, and analyzing the selected sample to determine a parameter thereof.

Preferably both oxygen concentration and carbon dioxide concentration are determined and breath-by-breath flow-weighted averages of the rates of oxygen consumption and carbon dioxide elimination are computed.

Other aspects and advantages of the present invention will become apparent from the following detailed description, taken in conjunction with the accompanying drawing, which illustrates by way of example the principles of the invention.

BRIEF DESCRIPTION OF THE DRAWING

The FIGURE is a fluid flow schematic of a metabolic monitor embodying the present invention.

DETAILED DESCRIPTION OF THE PREFERRED EMBODIMENT

Figure 1:
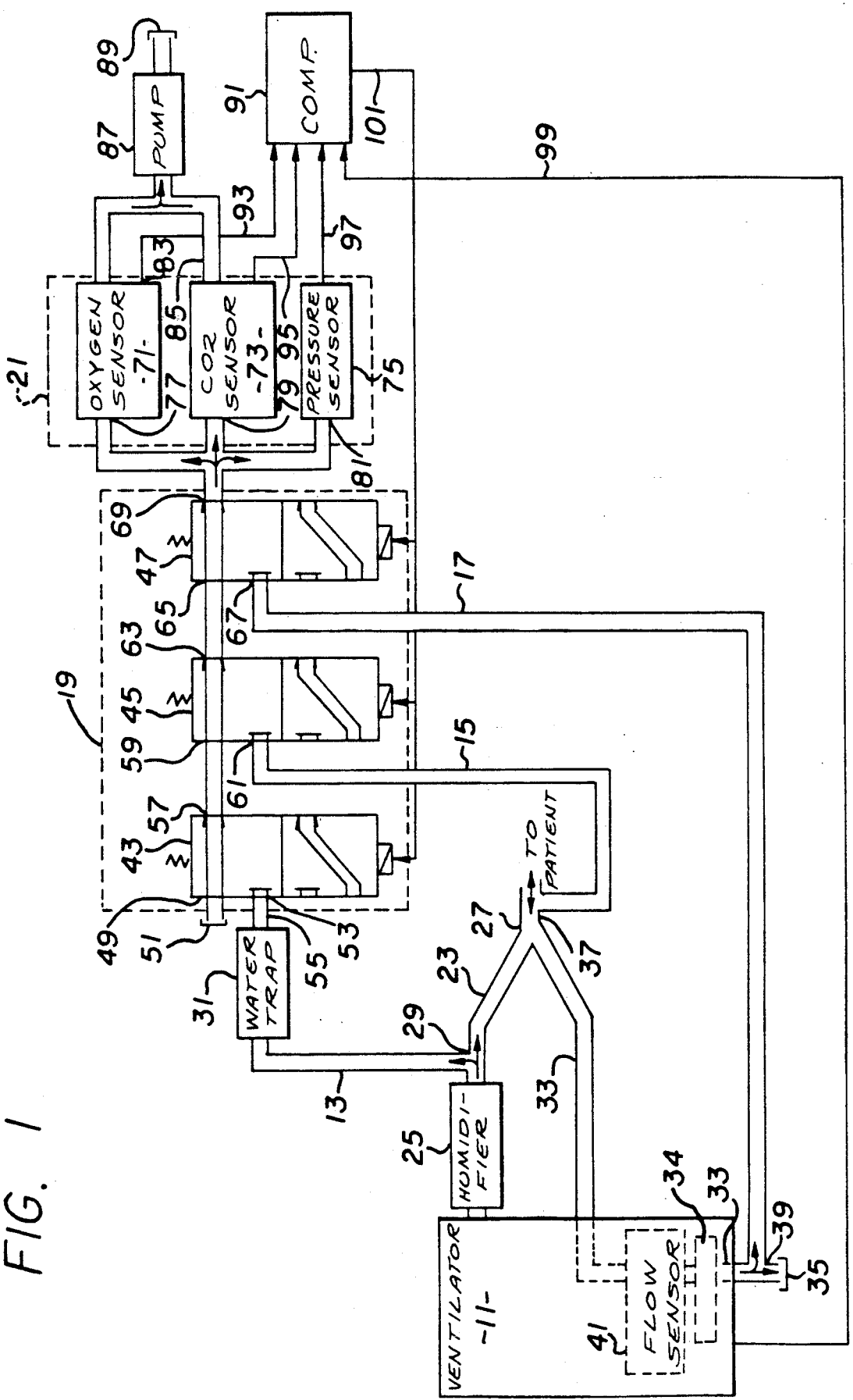

As shown in the drawing for purposes of illustration, the invention is embodied in a novel method and apparatus for monitoring metabolic rates of a patient intubated on a ventilator. Samples of inspiration and expiration gases are collected and analyzed to provide breath-by-breath rates of, for example, oxygen consumption and carbon dioxide elimination. Existing methods provide metabolic rates which are averaged over a number of breaths, but such averaged rates are not always adequate for modern medical treatment methods.

In accordance with the invention, an inspiration sample, an end-tidal expiration sample, and an ambient pressure expiration sample are collected. The ambient pressure sample is taken from a point prior to complete mixing of the gases exhaled in adjacent breaths and at a pressure which is essentially ambient room air pressure. Oxygen and carbon dioxide concentrations in the samples are determined and the rates of oxygen consumption and carbon dioxide elimination are calculated by flow weighted averages utilizing the ventilator flowmeters, thereby providing accurate breath-by-breath metabolic rates for use in medical diagnosis and treatment.

Turning now to the FIGURE, a metabolic monitor for providing metabolic data regarding a intubated patient receiving respiratory support on a ventilator 11 includes first, second and third sample conduits 13, 15 and 17, selector means generally designated 19 for selecting one of the gas samples for analysis, and sensor means generally designated 21 which provides a signal indicative of an unknown parameter of the select gas sample.

An inspiration conduit 23 carries inspiration gases from the ventilator 11 through a humidifier 25 to a patient wye 27. The patient wye 27 is adapted to provide the inspiration gases to, and to receive expiration gases from, the patient. The first sample conduit 13 is connected to the inspiration conduit 23 at a location 29 between the humidifier 25 and the wye 27 to collect a sample of the inspiration gases as provided by the ventilator 11. The first sample conduit 13 is preferably connected to a water trap 31 which traps any liquid water which gets into the first sample conduit 13.

An expiration conduit 33 carries expiration gases from the wye 27 through the ventilator 11 through exhalation valve 34 to an exhaust port 35. The second sample conduit 15 is connected to the patient wye 27 at a location 37 to collect an end-tidal sample of these expiration gases as exhaled by the patient. The third sample conduit 17, which collects an ambient pressure sample of the expiration gases, is connected to the expiration conduit 33 at a point 39 adjacent the port 35 at which there is no complete mixing of the gases exhaled in adjacent breathes and at a location after the exhalation valve such that the pressure is essentially ambient room air pressure.

The respirator 11 includes a flow sensor 41 in the expiration conduit 33 to provide a signal indicative of the flow rate of the gases in the expiration conduit 33.

The selector means 19 preferably includes a fluid flow control valve to establish fluid communication between the conduit which carries the selected sample and the sensor means 21. In the illustrative embodiment, the selector means 19 comprises first, second and third solenoid-activated valves 43, 45 and 47. The first valve 43 has a first input 49 which receives ambient air through a port 51 and a second input 53 which receives the inspiration sample through a conduit 55 from the water trap 31. An output 57 of the valve 43 is connected to a first input 59 of the second valve 45.

The second valve 45 has a second input 61 connected to the second sample conduit 15 and an output 63 connected to a first input 65 of the third valve 47. The third valve 47 has a second input 67 connected to the third sample conduit 17 and an output 69 connected to the sensor means 21.

The sensor means 21 preferably includes means such as an oxygen sensor 71 to sense oxygen concentration in the selected gas sample and a carbon dioxide sensor 73 to sense carbon dioxide concentration. A pressure sensor 75 which provides a signal indicative of the pressure of the selected sample is optionally included. Inputs 77, 79 and 81 of the sensors 71, 73 and 75, respectively, are connected to the output 69 of the third valve 47 to receive the selected gas sample. Outlets 83 and 85 of the sensors 71 and 73 are connected to a pump 87 which draws the sample through the sensors to an exhaust port 89.

Computer means such as a computer 91 is preferably provided to compute breath-by-breath flow weighted averages of the rates of oxygen consumption and carbon dioxide elimination by the patient. The computer 91 receives signals indicative of the oxygen and carbon dioxide concentrations from the sensors 71 and 73, as indicated by oxygen and carbon dioxide signal lines 93 and 95 extending from the sensors, 71 an 73, respectively, to the computer 91. The computer 91 also receives a pressure signal from the pressure sensor 75 as indicated by a pressure signal line 97 extending from the sensor 75 to the computer 91.

Means for providing a signal indicative of the flow rate of the exhalation gas from the patient is preferably also included as indicated by a flow sensor 41 and a flow rate signal line 99 extending from the ventilator 11 to the computer 91.

The computer 91 preferably includes means to control the selector means 19 as indicated by a control signal line 101 extending from the computer 91 to the solenoid valves 43, 45 and 47.

In operation, when the valve 47 is activated the sensors 71, 73 and 75 receive the ambient pressure sample from the third sample conduit 17 through the second input 67 of the valve 47. When the valve 45 is activated and provided the valve 47 is not activated the sensors receive the end-tidal sample from the second sample circuit 15 through the second input 61 of the valve 45. When the valve 43 is activated and provided the valves 45 and 47 are not activated the sensors receive the inspiration sample from the first sample conduit 13 through the second input 53 of the valve 43 and the first inputs 59 of the valve 45 and 65 of the valve 47.

If none of the valves 43, 45 and 47 is activated, the sensors receive ambient air through the port 51 and the first inputs 49, 59 and 65 of the three valves. Activation of first one and then another of the valves 43, 45 and 47 permits analysis of the various samples to determine the oxygen and carbon dioxide concentrations in each. This information, along with pressure information from the pressure sensor 75 and flow rate information from the flow sensor 41 in ventilator 11, is provided to the computer 91 as indicated by the various signal lines 93, 95, 97 and 99. The computer uses the information from the various sensors to compute breath-by-breath flow weighted average rates of oxygen consumption and carbon dioxide elimination.

The connection point 29 between the inspiration conduit 23 and the first sample conduit 13 is located between the humidifier 25 and the wye 27 because the volume of the humidifier acts as mixing chamber for delivered oxygen concentration. Most ventilators do not deliver a perfectly mixed concentration of inspiration gases, and inaccuracies can occur if the inspiration gases are sampled immediately after coming out of the ventilator.

The humidifier 25, in addition to serving as a mixing chamber, ensures a constant level of water vapor pressure in the inspiration sample independent of the humidity of any supply gas utilized by the ventilator 11. This is achieved by humidifying the gas above room temperature and then causing the gas to flow through a length of tubing such as that formed from a perfluorosulfonic acid membrane sold under the trademark "NAFION" which reduces the partial pressure of the water vapor to a level corresponding with ambient conditions of room temperature and relative humidity. Variations in these ambient conditions do not affect the accuracy of the sample analyses because the temperature and relative humidity of exhaled gas is also equilibrated to ambient conditions.

The connection point 29 is preferably located at least six inches upstream from the wye 27 to prevent inadvertent entry of any exhaled gases into the sample conduit 13.

The connection point 37 between the expiration conduit 33 and the second sample conduit 15 is located at the wye to permit accurate end-tidal measurements of carbon dioxide concentration in the exhaled gases.

The calculation of flow weighted averages depends on synchronization of the flow rate and concentration signals provided by the sensors. For the ambient pressure expiration sample this synchronization is a function of the transport delay time required for a molecule of the expiration gases to flow through the third sample conduit 17 to the sensor means 21, and this delay time is in turn a function of pressure. Keeping the pressure constant results in a constant delay time, and this in turn results in easy and accurate synchronization of the flow rate and concentration signals.

Ambient pressure conditions—which are relatively constant and in particular are not subject to rapid fluctuations—are found in the expiration conduit 33 downstream from an exhalation valve contained within the ventilator 11. Accordingly, the expiration sampling pressure in the third sample conduit 17 is kept constant by locating the connection point 39 downstream from said valve, thereby resulting in simple and accurate synchronization of the flow rate and concentration signals. If the connection point 39 were located upstream from the exhalation valve, pressure fluctuations would result in varying transport delay times. This in turn would necessitate dynamic measurement of pressure or flow in order to synchronize the flow and concentration signals, resulting in greater complexity of the monitor and increased risk of inaccuracy. Also, it should be noted that there should be no mixing chamber on the exhalation side of the patient tubing in order that breath-by-breath results be obtainable. If a mixing chamber were to be added for some other purpose, the sample location would need to be before that mixing chamber.

If the expiration gases flow through a mixing chamber before being sampled, breath-by-breath analysis is not possible. Accordingly, the connection point 39 should be located between the exhalation valve and any mixing chamber.

An incidental benefit to not utilizing a mixing chamber is the avoidance both of the bulk of such a chamber and of any need for sterilization of the chamber.

From the foregoing it will be appreciated that the method and apparatus of the invention provide accurate breath-by-breath flow weighted averages metabolic rates such as the rates of oxygen consumption and carbon dioxide elimination of a intubated patient on a ventilator. A metabolic monitor according to the invention can conveniently be connected to any of numerous kinds of ventilators. Moreover, there is no requirement for any mixing chamber in the expiration conduit, thereby avoiding the disadvantages inherent in the use of such devices.

Although a specific embodiment of the invention has been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

What is claimed is:

1. A metabolic monitor for providing metabolic rate data obtained from inspiration and expiration gases of a patient intubated on a ventilator having an inspiration conduit for providing the inspiration gases from the ventilator to the patient, an expiration conduit for conducting the expiration gases from the patient to the ventilator, said expiration conduit having an exhalation valve in fluid communication with the expiration conduit and an exhaust port of the ventilator in fluid communication with the ambient atmosphere and the exhalation valve for venting the expiration gases to the ambient atmosphere, the monitor comprising:

- a first sample conduit means in fluid communication with the inspiration conduit for collecting a sample of the inspiration gases as provided by the ventilator;
- a second sample conduit means in fluid communication with the expiration conduit for collecting an end-tidal sample of expiration gases as exhaled by the patient;
- a third sample conduit means in fluid communication with the exhalation valve and the exhaust port for collecting an ambient pressure sample of the expiration gases from a point prior to complete mixing of the gases exhaled in adjacent breaths and such that the pressure is essentially ambient room air pressure;
- selector means in fluid communication with the first, second and third sample conduit means for receiving said gas samples, and for selecting one of the gas samples for analysis; and
- sensor means in fluid communication with said selector means for receiving a selected one of said gas samples, and operative to provide a signal indicative of a parameter of the selected gas sample related to metabolic rate of the patient.

2. A metabolic monitor according to claim 1 wherein the parameter being indicated comprises oxygen concentration.

3. A metabolic monitor according to claim 1 wherein the parameter being indicated comprises carbon dioxide concentration.

4. A metabolic monitor according to claim 1 wherein the parameter being indicated comprises both oxygen and carbon dioxide concentrations.

5. A metabolic monitor according to claim 4 and further comprising means for providing a signal indicative of the flow rate of the exhaled patient gas and computer means responsive to the flow rate signal and the sensor signals to compute breath-by-breath flow weighted averages of the rates of oxygen consumption and carbon dioxide elimination by the patient.

6. The metabolic monitor according to claim 5 wherein the selector means comprises a fluid flow control valve operative to establish fluid communication between the conduit means which carries the selected sample and the sensor means.

7. A metabolic monitor according to claim 5 wherein the computer means includes means to control the selector means.

8. A metabolic monitor for providing metabolic data obtained from inspiration and exhaled gases of a patient intubated on a ventilator of the kind having an inspiration conduit that carries the inspiration gases to the patient, an exhaust port and an expiration conduit that carries the exhaled gases from the patient back through the ventilator to the exhaust port without completely mixing the gases exhaled in one breath with the gases exhaled in an adjacent breath, the expiration conduit having a first extremity adapted to receive the exhaled gases from the patient and a second extremity in fluid communication with the exhaust port, the monitor comprising:

- a first sample conduit means in fluid communication with the inspiration conduit for collecting a sample of the inspiration gases;
- a second sample conduit means in fluid communication with the expiration conduit adjacent the first extremity for collecting an end-tidal sample of the expired gases;
- a third sample conduit means in fluid communication with the expiration conduit adjacent the second extremity and operative to an ambient pressure sample of the expired gases;
- selector means in fluid communication with the first, second and third sample conduit means for receiving and for selecting one of the gas samples for analysis; and
- sensor means in fluid communication with said selector means for receiving a selected one of said gas samples and operative to provide a signal indicative of a parameter of the selected gas sample related to metabolic rate of the patient.

9. A metabolic monitor according to claim 8 wherein the parameter being indicated comprises oxygen concentration.

10. A metabolic monitor according to claim 8 wherein the parameter being indicated comprises carbon dioxide concentration.

11. A metabolic monitor according to claim 8 wherein the parameter being indicated comprises both oxygen carbon dioxide concentrations.

12. A metabolic monitor according to claim 11 and further comprising means for providing a signal indicative of the flow rate of the exhaled patient gas and computer means responsive to the flow rate signal and the sensor signals to compute breath-by-breath flow weighted averages of the rates of oxygen consumption and carbon dioxide elimination by the patient.

13. A metabolic monitor according to claim 12 wherein the selector means comprises a fluid flow control valve operative to establish fluid communication between the conduit means which carries the selected sample and the sensor means.

14. A metabolic monitor according to claim 13 wherein the computer means includes means to control the selector means.

15. A method of providing metabolic data obtained from inspiration and expiration gases of a patient intubated on a ventilator having an expiration conduit for receiving said expiration gases from the patient and an exhalation valve in said expiration conduit for venting said expiration gases to the ambient atmosphere, the method comprising:

- collecting a sample of said inspiration gases as provided by the ventilator;
- collecting an end-tidal sample of said expiration gases as exhaled by the patient;
- collecting an ambient pressure sample of the expiration gases from a point in said expiration conduit prior to complete mixing of the gases exhaled in adjacent breaths and after the exhalation valve such that the pressure is essentially ambient room air pressure;
- selecting one of the gas samples for analysis; and
- determining a parameter of the selected sample related to metabolic rate of the patient.

16. A method according to claim 15 wherein the step of determining a parameter comprises determining the concentration of oxygen in the sample.

17. A method according to claim 15 wherein the step of determining a parameter comprises determining the concentration of carbon dioxide in the sample.

18. A method according to claim 15 wherein the the step of determining a parameter comprises determining the concentration of both oxygen and carbon dioxide in the sample.

19. A method according to claim 18 and further comprising determining the exhaled patient gas flow rate data and computing breath-by-breath flow weighted averages of the rates of oxygen consumption and carbon dioxide elimination of the patient from the exhaled patient gas flow rate data and the oxygen and carbon dioxide concentration of the samples.

* * * * *

UNITED STATES PATENT AND TRADEMARK OFFICE
CERTIFICATE OF CORRECTION

PATENT NO. : 5,072,737  Page 1 of 2
DATED : December 17, 1991
INVENTOR(S) : Peter Goulding It is certified that error appears in the above-identified patent and that said Letters Patent is hereby corrected as shown below:

IN THE ABSTRACT:
    line 3, change "utilize" to --utilizing--.

Column 1, line 68, change "transistion" to --transition--.

Column 2, line 21, change "sterlize" to --sterilize--.

Column 3, lines 7-8, change "communicating" to --communication--.

Column 3, line 11, change "rates carried" to --rates is carried--.

Column 3, line 18, change "sample" to --samples--.

Column 3, line 61, change "a intubated" to --an intubated--.

Column 4, line 22, change "breathes" to --breaths--.

Column 5, line 16, change "circuit" to --conduit--.

Column 7, line 60, delete "an exhaust port"

Column 7, line 61, change "to the exhaust port without completely: to --to an exhaust port of the expiration conduit without completely--.

Column 8, line 10, change "and operative to" to --for collecting--.

UNITED STATES PATENT AND TRADEMARK OFFICE
CERTIFICATE OF CORRECTION

PATENT NO. : 5,072,737

DATED : December 17, 1991

INVENTOR(S) : Peter Goulding

It is certified that error appears in the above-identified patent and that said Letters Patent is hereby corrected as shown below:

Column 8, line 29, change "oxygen carbon dioxide" to
 --oxygen and carbon dioxide--.

Column 9, lines 4-5, change "wherein the the step" to
 --wherein the step--.

Signed and Sealed this

Eighth Day of June, 1993

*Attest:*

MICHAEL K. KIRK

*Attesting Officer*   *Acting Commissioner of Patents and Trademarks*